(12) United States Patent
Busta et al.

(10) Patent No.: US 7,447,298 B2
(45) Date of Patent: Nov. 4, 2008

(54) DECONTAMINATION AND STERILIZATION SYSTEM USING LARGE AREA X-RAY SOURCE

(75) Inventors: Heinz H. Busta, Park Ridge, IL (US); Stanley D. Lesiak, Naperville, IL (US)

(73) Assignee: Cabot Microelectronics Corporation, Aurora, IL (US)

(*) Notice: Subject to any disclaimer, the term of this patent is extended or adjusted under 35 U.S.C. 154(b) by 0 days.

(21) Appl. No.: 11/241,214

(22) Filed: Sep. 30, 2005

(65) Prior Publication Data
US 2006/0049359 A1 Mar. 9, 2006

Related U.S. Application Data

(63) Continuation-in-part of application No. 10/814,714, filed on Mar. 31, 2004.

(60) Provisional application No. 60/459,553, filed on Apr. 1, 2003.

(51) Int. Cl.
H01J 35/04 (2006.01)
(52) U.S. Cl. .......... 378/122; 378/64; 378/124
(58) Field of Classification Search .......... 378/64, 378/122, 124
See application file for complete search history.

(56) References Cited

U.S. PATENT DOCUMENTS

| | | | |
|---|---|---|---|
| 1,981,583 A * | 11/1934 | Craig | 426/234 |
| 3,928,765 A | 12/1975 | Teller | |
| 4,531,122 A | 7/1985 | Redfield | |
| 4,670,894 A | 6/1987 | Birnbach et al. | |
| 4,983,849 A | 1/1991 | Thompson et al. | |
| 4,998,268 A * | 3/1991 | Winter | 378/63 |
| 5,245,686 A | 9/1993 | Faris et al. | |
| 5,482,726 A | 1/1996 | Robinson, Jr. | |
| 5,498,925 A | 3/1996 | Bell et al. | |
| 5,529,524 A | 6/1996 | Jones | |
| 5,548,181 A | 8/1996 | Jones | |
| 5,577,090 A | 11/1996 | Moses | |

(Continued)

FOREIGN PATENT DOCUMENTS

WO   WO 02/075771   9/2002

OTHER PUBLICATIONS

Hudson Research, Inc., Flash X-ray Irradiator, 2001.*

(Continued)

*Primary Examiner*—Chih-Cheng G Kao
(74) *Attorney, Agent, or Firm*—Thomas E. Omholt; Phillip M. Pippenger; Steven D. Weseman

(57) ABSTRACT

A novel x-ray treatment system utilizes one or more large area flat panel sources of x-ray radiation directed into a target zone. A target substance within the target zone is irradiated with x-ray radiation from the one or more flat panel sources, reducing the biological effects of a contaminant presence therein. The flat panel source comprises an electron source, an electron accelerator, and an electron target medium. The electron source may emit electrons either via field emission or thermionic emission. The x-ray source may operate in transmissive, reflective, or combined transmissive/reflective mode. The use of large area flat panel x-ray sources in the inventive systems allows for decreased installation and operational costs as well as increased efficiency.

20 Claims, 9 Drawing Sheets

U.S. PATENT DOCUMENTS

| | | | |
|---|---|---|---|
| 5,578,901 A | 11/1996 | Blanchet-Fincher et al. | |
| 5,587,623 A | 12/1996 | Jones | |
| 5,606,588 A | 2/1997 | Umstadter et al. | |
| 5,614,781 A | 3/1997 | Spindt et al. | |
| 5,616,368 A | 4/1997 | Jin et al. | |
| 5,619,097 A | 4/1997 | Jones | |
| 5,623,180 A | 4/1997 | Jin et al. | |
| 5,667,724 A | 9/1997 | Petersen | |
| 5,688,158 A | 11/1997 | Jones et al. | |
| 5,691,600 A | 11/1997 | Moyer et al. | |
| 5,709,577 A | 1/1998 | Jin et al. | |
| 5,746,635 A | 5/1998 | Spindt et al. | |
| 5,747,100 A | 5/1998 | Petersen | |
| 5,770,918 A | 6/1998 | Kawate et al. | |
| 5,779,920 A | 7/1998 | Chadha et al. | |
| 5,796,211 A | 8/1998 | Graebner et al. | |
| 5,821,685 A | 10/1998 | Peterson | |
| 5,838,096 A | 11/1998 | Shinada et al. | |
| 5,926,239 A | 7/1999 | Kumar et al. | |
| 5,949,849 A * | 9/1999 | Hirano et al. | 378/121 |
| 5,977,697 A | 11/1999 | Jin et al. | |
| 5,982,095 A | 11/1999 | Jin et al. | |
| 5,989,776 A | 11/1999 | Felter et al. | |
| 6,005,247 A | 12/1999 | Baum | |
| 6,007,963 A | 12/1999 | Felter et al. | |
| 6,020,677 A | 2/2000 | Blanchet-Fincher et al. | |
| 6,057,637 A | 5/2000 | Zettl et al. | |
| 6,064,148 A | 5/2000 | Tolt et al. | |
| 6,068,750 A | 5/2000 | Rasmussen | |
| 6,097,139 A | 8/2000 | Tuck et al. | |
| 6,115,453 A | 9/2000 | Hell et al. | |
| 6,117,294 A | 9/2000 | Rasmussen | |
| 6,132,492 A | 10/2000 | Hultquist et al. | |
| 6,146,230 A | 11/2000 | Kim et al. | |
| 6,146,798 A | 11/2000 | Bringans et al. | |
| 6,162,577 A | 12/2000 | Felter et al. | |
| 6,195,411 B1 | 2/2001 | Dinsmore | |
| 6,239,547 B1 | 5/2001 | Uemura et al. | |
| 6,250,984 B1 | 6/2001 | Jin et al. | |
| 6,327,338 B1 | 12/2001 | Golovanivsky et al. | |
| 6,333,968 B1 | 12/2001 | Whitlock et al. | |
| 6,346,776 B1 | 2/2002 | Robinson et al. | |
| 6,459,089 B1 * | 10/2002 | Masefield et al. | 250/453.11 |
| 6,463,123 B1 * | 10/2002 | Korenev | 378/69 |
| 6,504,898 B1 | 1/2003 | Kotler et al. | |
| 6,553,096 B1 | 4/2003 | Zhou et al. | |
| 6,556,651 B1 | 4/2003 | Thomson et al. | |
| 6,556,654 B1 * | 4/2003 | Hansen et al. | 378/101 |
| 6,556,656 B2 | 4/2003 | Hess et al. | |
| 6,583,423 B2 * | 6/2003 | Rose | 378/69 |
| 6,628,745 B1 | 9/2003 | Annis et al. | |
| 6,674,837 B1 | 1/2004 | Taskar et al. | |
| 6,692,694 B1 * | 2/2004 | Curry et al. | 422/28 |
| 6,713,773 B1 | 3/2004 | Lyons et al. | |
| 6,738,451 B2 | 5/2004 | Avnery | |
| 6,750,461 B2 | 6/2004 | Fink et al. | |
| 6,760,407 B2 | 7/2004 | Price et al. | |
| 6,765,987 B2 | 7/2004 | Fleming et al. | |
| 6,806,629 B2 | 10/2004 | Sung | |
| 6,821,175 B1 * | 11/2004 | Tuck et al. | 445/24 |
| 6,844,557 B2 * | 1/2005 | Miller | 250/453.11 |
| 6,850,595 B2 * | 2/2005 | Zhou et al. | 378/122 |
| 6,868,136 B2 | 3/2005 | Hansen et al. | |
| 6,876,724 B2 | 4/2005 | Zhou et al. | |
| 6,931,095 B1 | 8/2005 | Koenck et al. | |
| 2002/0009179 A1 | 1/2002 | Hess et al. | |
| 2002/0085674 A1 * | 7/2002 | Price et al. | 378/122 |
| 2002/0094064 A1 * | 7/2002 | Zhou et al. | 378/122 |
| 2002/0191739 A1 | 12/2002 | Allen et al. | |
| 2003/0002628 A1 | 1/2003 | Wilson et al. | |
| 2003/0039726 A1 | 2/2003 | Yuan | |
| 2003/0128807 A1 * | 7/2003 | Kotler et al. | 378/64 |
| 2004/0022665 A1 | 2/2004 | Lu | |
| 2004/0150311 A1 | 8/2004 | Jin | |
| 2004/0198892 A1 | 10/2004 | Busta et al. | |
| 2005/0067935 A1 | 3/2005 | Lee et al. | |
| 2005/0074093 A1 | 4/2005 | Kindlein et al. | |
| 2005/0084572 A1 | 4/2005 | Lindsay et al. | |
| 2005/0167368 A1 | 8/2005 | Gehringer et al. | |

OTHER PUBLICATIONS

Hudson Research, Inc., Flash X-ray Irradiator [online], 2001 [retrieved from Dec. 8, 2002]. Retrieved from the Internet:<URL:http://web.archive.org/web/20021208082049/http://www.hudsonresearch.com/fxi.html>.*

Karabutov et al., *Proceedings of the 14th International Vacuum Microelectronics Conference*:277-278 (Aug. 12-16, 2001).

* cited by examiner

DECONTAMINATION AND STERILIZATION SYSTEM USING LARGE AREA X-RAY SOURCE

CROSS-REFERENCE TO RELATED APPLICATIONS

This patent application is a continuation-in-part of copending U.S. patent application Ser. No. 10/814,714, filed Mar. 31, 2004, by Busta et. al, entitled "Electron Source And Method For Making Same," which application is herein incorporated by reference in its entirety.

FIELD OF THE INVENTION

This invention relates generally to x-ray generation and use, and, more particularly, relates to a large area source for generating x-ray radiation and a system for using same to decontaminate and/or sterilize a target material.

BACKGROUND

High-energy electromagnetic radiation in the form of x-rays is used in many areas today. Although the use of x-rays in medical imaging is the most familiar setting to most people, other uses abound as well. For example, x-rays may be used in a medical setting for purposes of activation, such as of a medication or substance, rather than for imaging. Moreover, many uses of x-ray radiation in ground and geological exploration are known, such as in connection with oil exploration or subsurface imaging. One effective use of x-ray radiation is in the treatment of substances to reduce the impact of biological and other contamination. For example, food can be irradiated to kill microorganisms, making the food safer to consume. Waste water or runoff may be irradiated in the same manner to reduce the effects of contamination.

However, as useful as x-rays are in some of these capacities, the efficiency with which that radiation is produced and directed is suboptimal at present. Typical x-ray sources comprise a point source electron producer, an accelerator, and a metal target. In operation, the electrons generated by the point source are accelerated through the accelerator, and impact the metal target. Upon impact of the high-energy electrons with the target, x-ray radiation is emitted.

Typically the emitted radiation spreads in a conical pattern beyond the region of impact depending upon the composition and configuration of the target, the energy and dispersal of the impinging electrons, etc. Given this divergent radiation pattern, it can be seen that the radiation dose at a given distance r from the region of impact falls off in approximately an inverse squared ($1/r^2$) manner. To effectively employ this radiation pattern at proper doses, a strong radiation field, accounting for the fall off with distance, must be generated, and the object of interest must be positioned properly in the radiation cone. Although some radiation sources use multiple point sources, or one or more mobile point sources, to make up for the suboptimal emission pattern, such systems have their own inherent drawbacks and complexities. In particular, complications involving source timing, positioning, etc. are commonplace.

In the treating of materials for decontamination or sanitation purposes in particular, it is important to be able to deliver a uniform and sufficiently strong radiation pattern so as to avoid overly degrading the target material while ensuring adequate radiation to reduce the impact of microorganisms (or larger organisms) and contaminants. Moreover, it is important for commercialization that the x-ray source has adequate power efficiency to reduce the costs of use. Present systems fall short in one or more of these areas. Accordingly, there is a need for an x-ray treatment system that improves over the prior art systems at least in terms of efficiency and uniformity of field.

BRIEF SUMMARY OF THE INVENTION

Embodiments of the invention provide a novel technique for x-ray generation and use. In particular, the treatment system described herein utilizes, according to an embodiment of the invention, one or more large area flat panel sources of x-ray radiation directed into a target zone. A target substance to be treated is placed within the target zone, such as via conveyor belt, pipe, etc., and is irradiated with radiation from the one or more flat panel sources to reduce the biological effects of the contaminant presence in the target substance.

The flat panel source according to an embodiment of the invention comprises an electron source, an electron accelerator, and an electron target medium. Electrons are extracted or emitted from the electron source and are accelerated toward the electron target medium. The impact of the accelerated electrons upon the target medium causes the emission of x-ray radiation. The electron source may be of any suitable material and configuration. For example, the electron source may emit electrons either by a process of field emission or by a process of thermionic emission.

The use of large area flat panel x-ray sources in the inventive systems allows for decreased installation and operational costs as well as increased efficiency. Additional features and advantages of the invention will be made apparent from the following detailed description of illustrative embodiments which proceeds with reference to the accompanying figures.

BRIEF DESCRIPTION OF THE DRAWINGS

While the appended claims set forth the features of the present invention with particularity, the invention, together with its objects and advantages, may be best understood from the following detailed description taken in conjunction with the accompanying drawings of which:

DETAILED DESCRIPTION

The invention pertains to x-ray generation and use, and encompasses, in embodiments of the invention, a novel system and technique for treating a target substance such as a food item, water, or other material, such as for purposes of decontamination or sterilization. In general overview, an architecture according to an example embodiment of the invention comprises one or more flat panel sources of x-ray radiation adjacent to and/or surrounding a target zone (volume). A target substance is placed within the target zone and is irradiated with radiation from the flat panel source(s) to reduce the effects of contaminants in the target substance. The target substance may reside stationarily within the target zone or may be passed, such as via conveyer, or flowed, such as via radiation transparent tubing, through the zone.

The systems according to embodiments of the invention are useful for rendering harmless both biological and chemical contaminants in the target substance. For example, if the contaminant is bacterial, fungal or viral, the system can be used to kill an amount of the contaminant sufficient to substantially reduce a risk of infection in a consumer of the target substance, or substantially reduce (defer or prevent) spoilage of the target substance. If the contaminant is chemical, the system can be used to chemically modify (e.g., destroy or inactivate) an amount of the contaminant sufficient to substantially reduce a risk of a toxic reaction in a consumer of the target substance.

Figure 1:
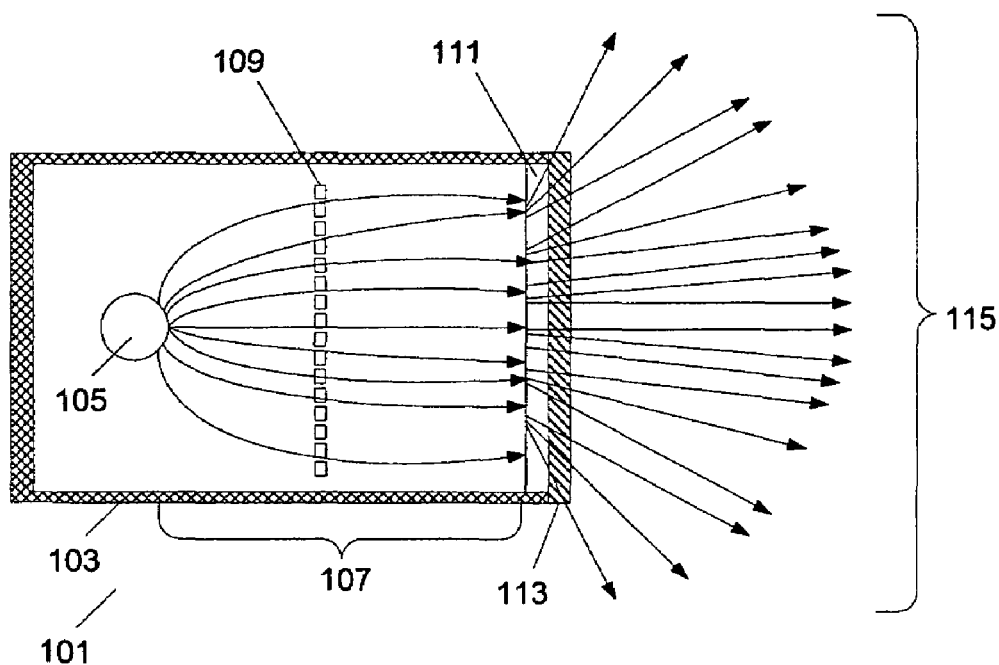
FIG. 1 is a cross-sectional side view of a prior art x-ray generation apparatus.

Before discussing the details of embodiments of the invention, a brief discussion of a generalized prior art system will be presented for the convenience of the reader. Referring to FIG. 1, a prior art x-ray source is shown, isolated from any application. The source 101 comprises an envelope 103. The envelope 103 is typically evacuated at least partially to minimize collisions between electrons and gas phase molecules. The source 101 further comprises an electron source 105. The electron source 105 generates electrons 107 such as via thermal extraction. A portion of the electrons 107 are electrostatically accelerated by a field applied by an accelerator grid 109 and traverse the envelope 103 to impact upon a target material 111. The electron impact with the target material produces an emission of x-ray radiation, a portion 115 of which is directed toward and passes through window 113 or other outlet.

Figure 2:
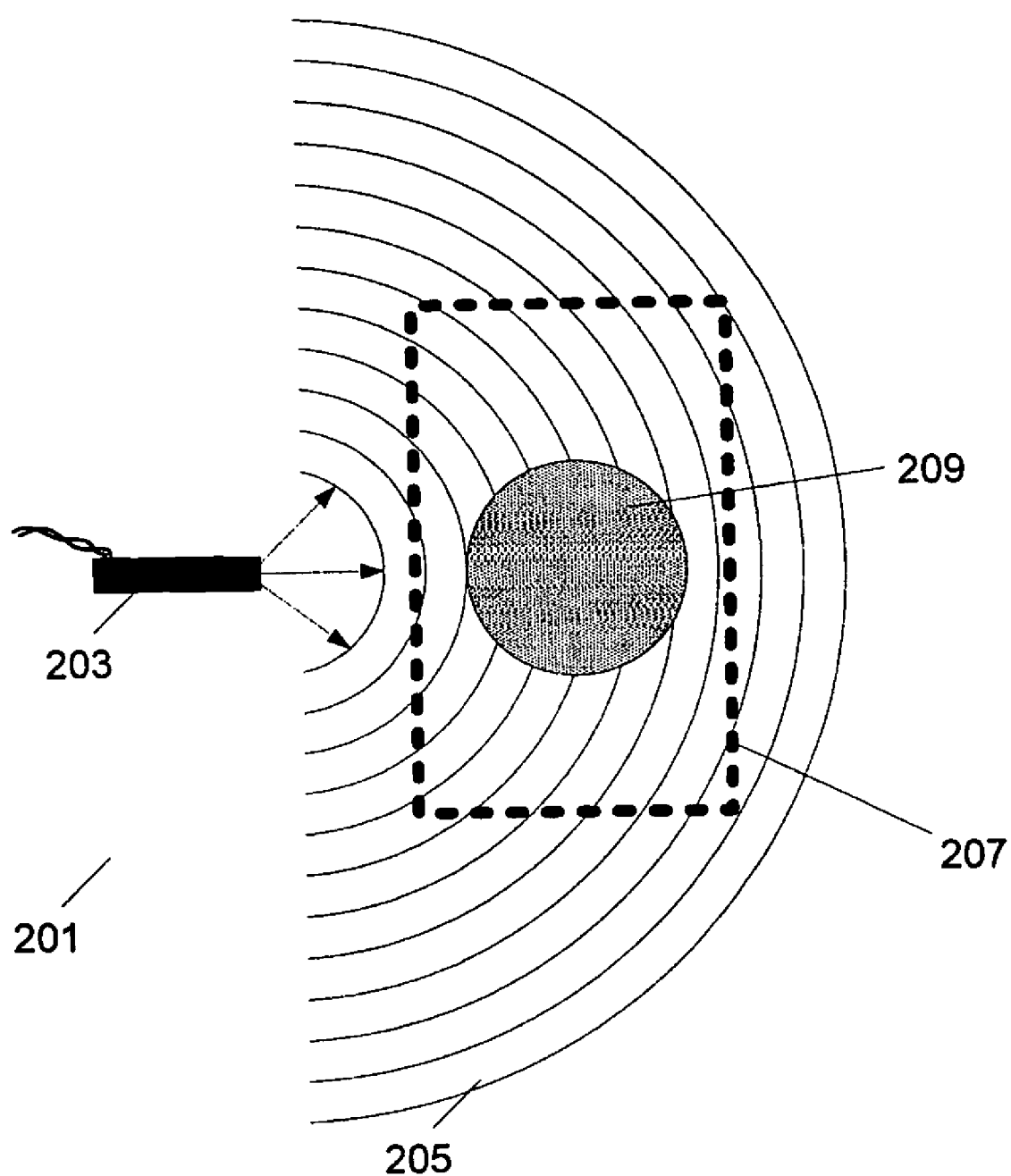
FIG. 2 is a schematic top view of a prior art material x-ray treatment system using a point source x-ray device.

FIG. 2 illustrates, in schematic view, a substance treatment system according to the prior art. The system 201 comprises a point x-ray source 203 such as that described with respect to FIG. 1. The x-ray source 203 emits a hemispherical pattern of radiation 205. The system 201 is configured such that the emitted radiation 205 impinges upon a target zone 207 containing a target substance 209, thereby irradiating the target substance 209. As will be appreciated, the resultant irradiation is very non-uniform. Moreover, the radiation pattern 205 resulting from the point source 203 produces considerable inefficiencies in the system 201.

While it will be appreciated that a point x-ray source emits radiation from a surface rather than an actual point, at any appreciable distance from such a source, the pattern appears substantially to diverge from a common point or small volume. The radiation from such sources diverges in a spherical manner, dropping off proportionally to the inverse square of distance. Thus, assuming that the source 203 is essentially a point source and the target zone 207 is 1 m$^2$, the usable intensity of the source 203 is 1 m$^2$/4$\pi$d$^2$. If the zone 207 is 2.5 meters from the source 203, this results in a factor of 1/78. Thus, the divergent nature of the point source radiation yields an efficiency of only about 1.3% (i.e., a loss of almost 99%). This inefficiency means that the power output of the source must be such that the remaining power at the target zone is sufficient. Consequently, expensive power supplies are needed to operate such a system. In addition to the costs of such support equipment, the operational energy costs of such a system are quite high due to the inefficiencies of the point source.

Embodiments of the invention address the shortcomings of prior systems and provide an efficient and low cost system for treating food and other substances with radiation for purposes of sanitation, decontamination, etc. Embodiments of the invention will now be described in greater detail with reference to the accompanying drawings. A flat x-ray source according to an embodiment of the invention will be first described, followed by a discussion of the flat panel x-ray sources employed in various embodiments.

A flat panel x-ray source usable within embodiments of the invention in described in U.S. Patent Application Ser. No. 2004/0198892 A1, entitled "Electron source and method for making same," filed Mar. 31, 2004, by Busta et al. Although the aforementioned application Ser. No. 2004/0198892 A1 is noted here for its discussion of flat panel electron and x-ray sources, its teachings are not so limited, and it is herein incorporated by reference in its entirety for all that it teaches, shows, describes, and makes known, without any exclusion of any portion, express or implied, of the application.

Figure 3:
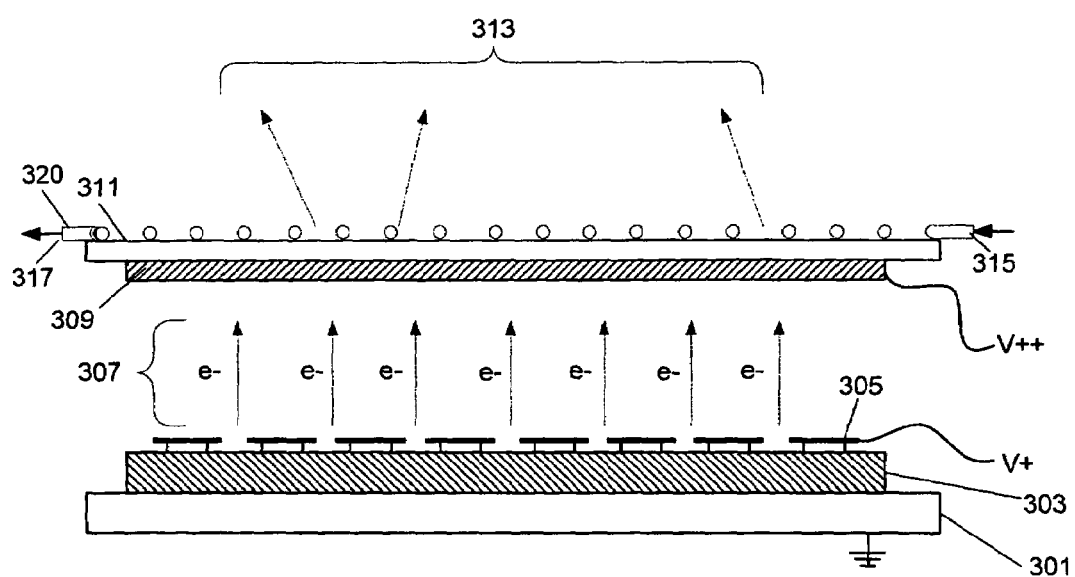
FIG. 3 is a cross-sectional side view of an x-ray generation apparatus usable within an embodiment of the invention, having a transmissive mode large area flat panel x-ray source having a field emission electron source.

One transmissive mode flat panel source usable within embodiments of the invention is generally as shown in FIG. 3. In broad terms, the flat panel source comprises an electron source, an electron accelerator, and a target medium, with the impact of the accelerated electrons upon the target medium causing the emission of x-ray radiation. Referring more specifically to the illustrated embodiment of the flat panel shown in FIG. 3, a substrate 301 supports an electron source composition 303. The electron source composition 303 comprises a substance or material that allows the field emission of electrons therefrom. Exemplary compositions are described in the abovementioned patent application.

In order to extract electrons 307 from the electron source composition 303, an electron extraction grid 305 is positioned near to but substantially electrically isolated from the electron source composition 303. The electron extraction grid 305 is maintained at a voltage V+ relative to the electron source composition 303 that is sufficient to extract electrons from the electron source composition 303 under the field effect. A target material 309 is positioned so that it is generally in the path of a substantial number of the extracted electrons 307. Moreover, the target material 309 is maintained at a potential V++ that is positive with respect to both the electron extraction grid 305 potential and the electron source composition 303 potential. In this manner, the extracted electrons are accelerated toward the target material 309.

The target material 309 may be any of a number of suitable materials as will be appreciated by those of skill in the art. Suitable materials are those for which the electron energies generated by the particular voltages and spacings used is sufficient to cause x-ray emission from the target material 309. Suitable materials include, for example, Cu, W, Mo, etc. This layer may be deposited by vapor deposition, sputtering, plating, etc., or may be placed, such as in the form of a foil.

Upon striking the target material 309, at least a small portion of the electrons 307 result in the emission of x-ray radiation from the target material 309. A portion 313 of this generated radiation will be directed outwardly, i.e. in generally the same direction as the electrons 307 were accelerated. In a preferred embodiment of the invention, the support surface 311 for the target material 309 is transparent to x-rays, and thus the portion 313 exits the device.

Although not shown, the space through which the electrons are accelerated is preferably at least partially evacuated to maximize the portion of electrons that travel ballistically without collisions with gas molecules. Collisions with gas molecules are undesirable in that such collisions reduce the effective electron yield and hence reduce the efficiency of the x-ray generation system. Moreover, the impact of electrons with gas molecules can result in the generation of positive ions, which are then accelerated back toward the electron extraction grid 305 and the electron source composition 303, potentially causing damage or premature wear.

Figure 4:
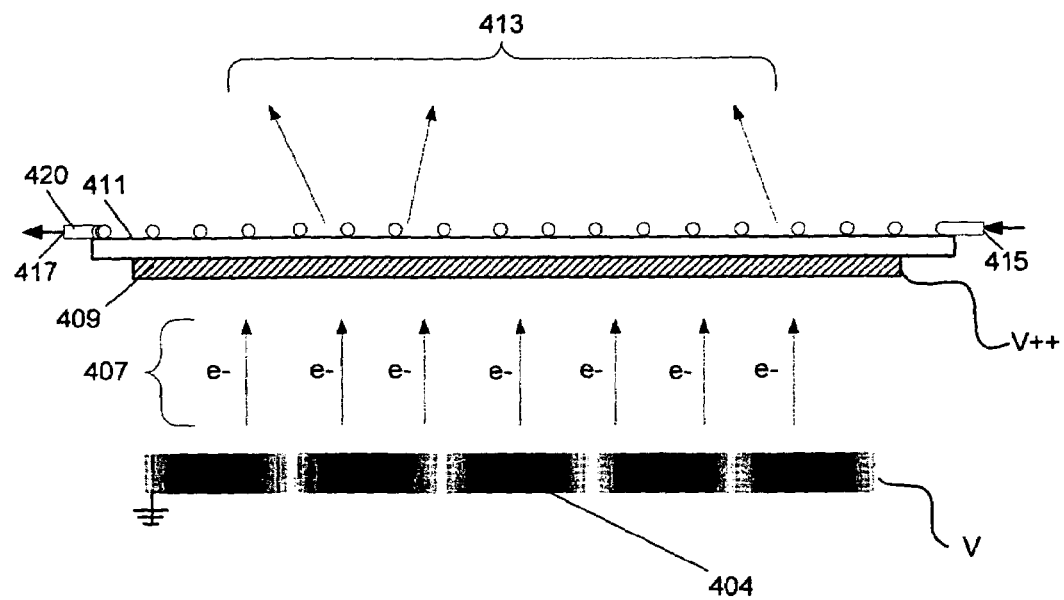
FIG. 4 is a cross-sectional side view of an x-ray generation apparatus usable within an embodiment of the invention, having a transmissive mode large area flat panel x-ray source having a thermionic emission electron source.

An alternative transmissive mode flat x-ray panel source usable within embodiments of the invention is shown schematically in FIG. 4. The device of FIG. 4 is similar to that of FIG. 3, with the exception that the electron source composition 303 and extraction grid 305 have been replaced by a thermionic emissive element 404 such as a ribbon or wire of material. Although the thermionic emissive element 404 is shown from the side, it will be appreciated that the element 404 is wound or run such that its correspondence with the target material 409 is substantially uniform. That is, although the element 404 may have a lateral area corresponding to a small fraction of the lateral area of the target material 409 (i.e. in the flat dimension of the panel, perpendicular to the plane of FIG. 4), each portion, such as each eighth, of the target material 409 vertically corresponds with approximately the same fraction of the element 404 as each other portion of the target material 409. This provides relative uniformity in the lateral distribution of emitted electrons 407 and promotes efficient use of the element 404 and the target material 409. Typically, the element 404 is wound or wrapped in a serpentine pattern, with the number of passes in a given distance being determined by the scale on which uniformity is desired. For example, the use of a three-pass configuration would yield approximate uniformity on a very rough scale, whereas the use of a 91-pass configuration over the same target material 409 area would yield substantially greater uniformity.

Suitable materials for thermionic emission will be known to those of skill in the art, but typical materials are Thoriated Tungsten and Lanthanum Hexaboride. In general, suitable materials include without limitation graphite, metal, or metal alloys, or nonmetal alloys, or combinations of these.

Although the devices described above with respect to FIGS. 3 and 4 are transmissive mode devices, the invention is not so limited. In alternative embodiments of the invention, other modes are used. Thus, in general, exemplary modes of operation are (1) Field Emission Transmissive (shown in FIG. 3); (2) Field Emission Reflective; (3) Thermionic Emission Transmissive (shown in FIG. 4); and (4) Thermionic Emission Reflective. The reflective mode utilizes x-ray radiation that emerges from the target material 309, 409 on the same side as the electron impact as opposed to the opposite side (as in transmissive mode). For reflection mode, the target material is substantially thicker than for the transmissive mode.

The configuration of the illustrated x-ray generation apparatuses generate electrons over a wide area and provide x-ray radiation over a much larger area than point source devices. For example, the illustrated devices can easily emit x-rays from an area of 100 square inches or greater.

Due to the high power required for rapid food and substance sanitation and/or decontamination, and the relative inefficiency of converting electrons to x-ray radiation 313, 413, devices such as those described by way of FIG. 3 and FIG. 4 generate a substantial amount of heat. If this heat is not removed from the system, damage or accelerated wear may result. Thus, in a preferred embodiment of the invention, the flat panel x-ray generation device includes a cooling mechanism. For smaller applications, low power cooling such as via solid state coolers may be used. However, more cooling power is typically required, and in such cases a liquid heat removal system is used.

In an embodiment of the invention, the liquid heat removal system comprises a coiled fluid path housed in a thermally conductive conduit, the conduit being in thermal contact with the target material 309, 409 such as via support surface 311, 411. In FIGS. 3 and 4, the conduit 320, 420 is shown in cross section, with fluid inlet 315, 415 and fluid outlet 317, 417.

Figure 5:
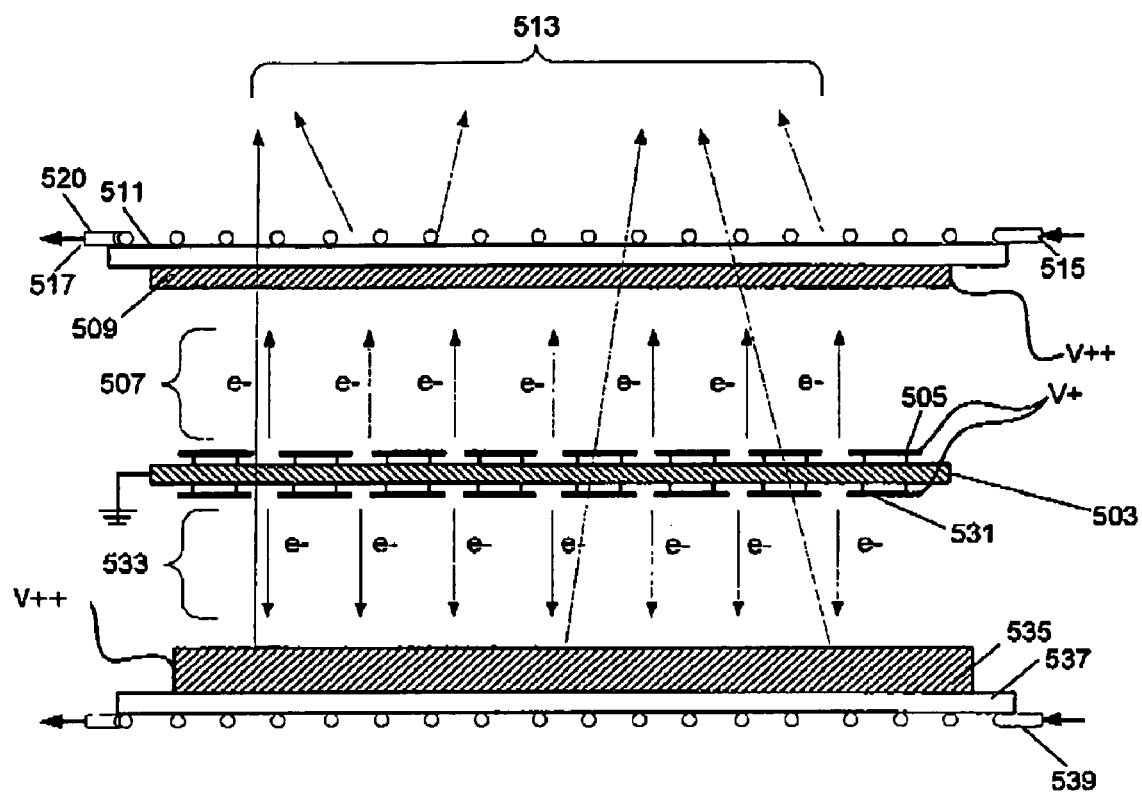
FIG. 5 is a cross-sectional side view of an x-ray generation apparatus usable within an embodiment of the invention, having a large area flat panel x-ray source having a field emission electron source and operating in a combined reflective and transmissive mode.

The efficiency of the described x-ray generation system may be increased by employing both reflective and transmissive mode operation. Although the device shown in FIG. 5 utilizes field emission to provide electrons, a thermionic element may be alternatively or additionally used to supply electrons. The illustrated device is similar to that shown in FIG. 3, and like elements are similarly numbered in the last two digits.

The illustrated device differs from that of FIG. 3 in that an additional oppositely facing extraction grid 531 is provided. The second extraction grid 531 extracts electrons 533 which are accelerated toward a second target surface 535 under the influence of an applied field between the extraction grid 531 and the target surface 535. Upon impact of the electrons 533 with the target surface 535, x-rays are generated, a portion of which are directed back toward the grid. Depending on the thickness of the target surface 535, a portion of these x-rays traverse the device and exits the device with the portion of x-rays yielded by the transmissive portion of the device. It will be appreciated that although support structure 511 should be x-ray transmissive, the support surface 537 need not be. In an embodiment of the invention, the surface 537 blocks and/ or reflects x-rays rather than transmitting them. The support 537 may similarly be equipped with a cooling mechanism 539 to remove waste heat and enhance device operation and longevity.

It should be noted that each embodiment uses more common elements for the electron source (i.e., Tungsten, Carbon Black, etc.) as described above and in the incorporated application. This provides a cost and simplicity advantage over systems that utilize more exotic materials such as nanotubes. However, in an embodiment of the invention such exotic materials may be used alternatively or additionally. Moreover, unlike some systems, the electrons of the illustrated system travel ballistically, without focusing, in order to provide the wide area operation shown.

Figure 6:
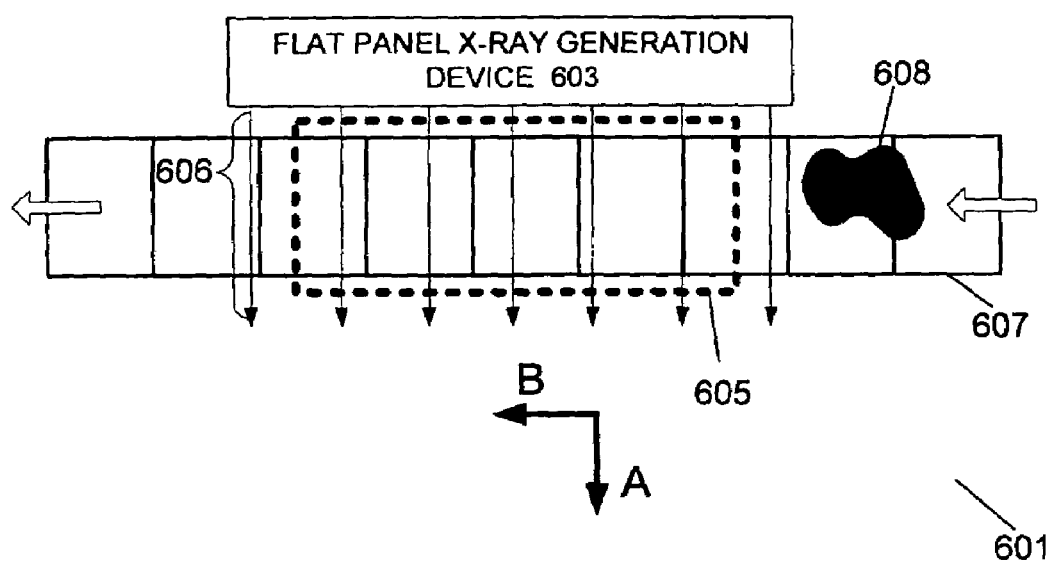
FIG. 6 is a schematic top view of an x-ray treatment system according to an embodiment of the invention, wherein a conveyor is used to transport non-liquid target material.

Having described a number of x-ray generation apparatus usable within embodiments of the invention, some exemplary uses of such systems will now be discussed. FIG. 6 illustrates schematically an irradiation system for the sanitation and/or decontamination of solid or semi-solid (i.e., non-liquid) materials. The system 601 comprises an x-ray generation device 603 as described above for irradiating a target zone 605 with x-ray radiation 606. The target zone 605 may be superimposed on a conveyor belt 607 or other transport mechanism to simplify the introduction of material 608 into the target zone 605 for treatment.

The width and height dimensions of the target zone 605 perpendicular to the emitted radiation (i.e., in direction B and out of page dimension) are preferably selected so as to extend across the face of the x-ray generation device 603 within a region of the radiation field 606 that is relatively uniform, e.g., with less than approximately 20% variation. The dimensions of the target zone 605 in direction A (i.e., parallel to the emitted radiation) are preferably selected based upon the absorption and needed dose for the material to be treated 608. For example, highly absorptive materials 608 may require a shallower target zone 605 to assure suitable penetration of the radiation 606. Moreover, a higher dose requirement may affect both the dwell time in the zone 605 and the depth of the zone 605 in direction A.

The optional conveyor belt 607 may be continually moving so that the material to be treated 608 has a certain dwell time within the field emitted by the x-ray generation device 603. Alternatively, the conveyor 607 may step material through in increments approximately equal to the target zone 605 width dimension in direction B, with each step followed by a delay as necessary to allow for the treatment of the material 608 within the target zone 605.

Figure 7:
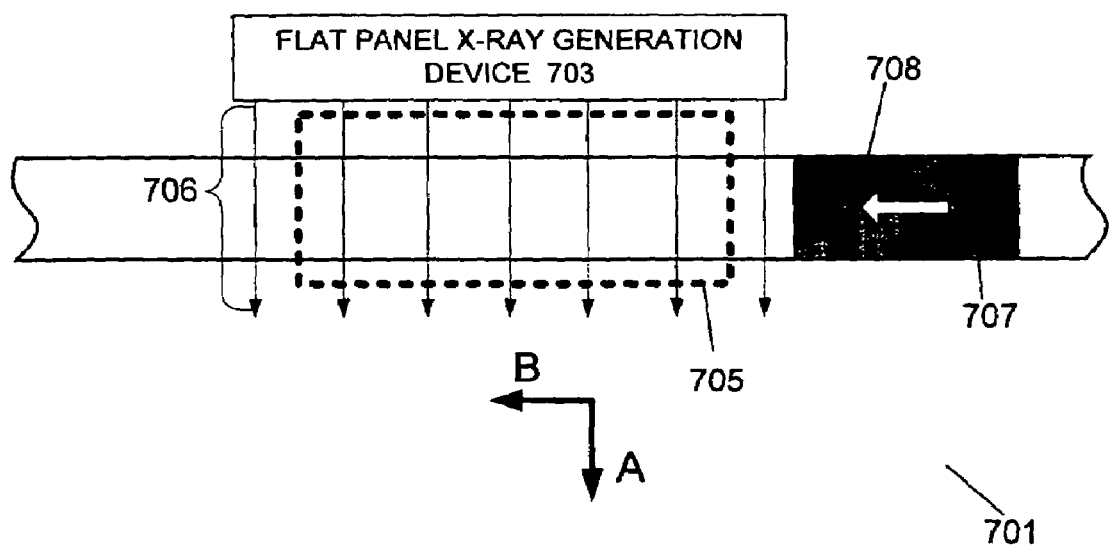
FIG. 7 is a schematic top view of an x-ray treatment system according to an embodiment of the invention, wherein a conduit is used to transport liquid or gas target material.

Alternatively, liquid or gaseous materials may be treated within embodiments of the invention. In particular, FIG. 7 illustrates schematically an irradiation system for the sanitation and/or decontamination of liquid and/or gaseous materials. The system 701 comprises an x-ray generation device 703 as described above for irradiating a target zone 705 with x-ray radiation 706. In this case, the target zone 705 is superimposed on a conduit 707 of substantially x-ray transparent material to introduce material 708 into the target zone 705 for treatment.

Figure 8A:
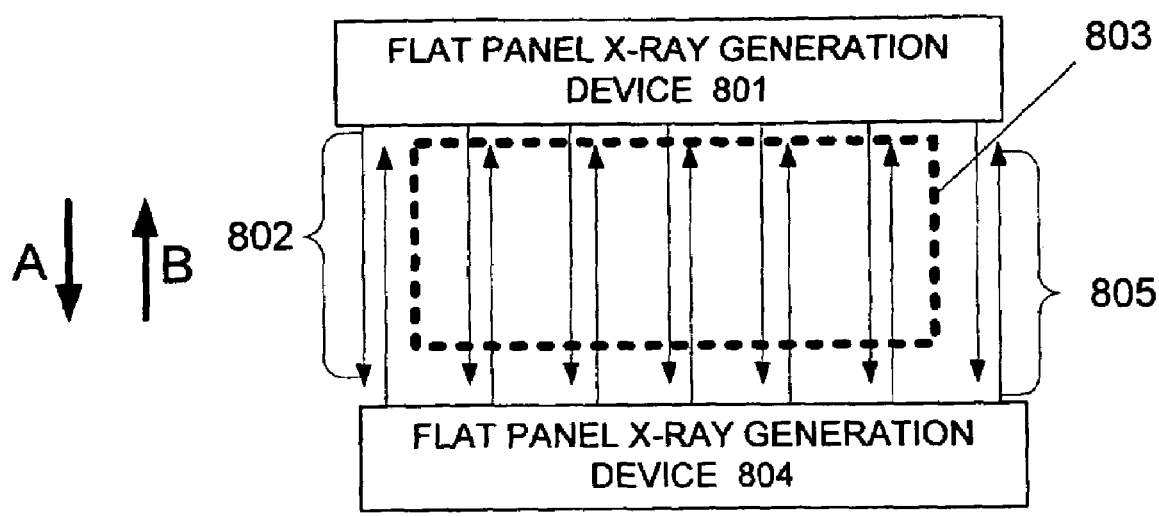
FIG. 8a is a schematic top view of an x-ray treatment system according to an alternative embodiment of the invention, within which an opposing pair of large area flat panel x-ray sources are used.
Figure 8B:
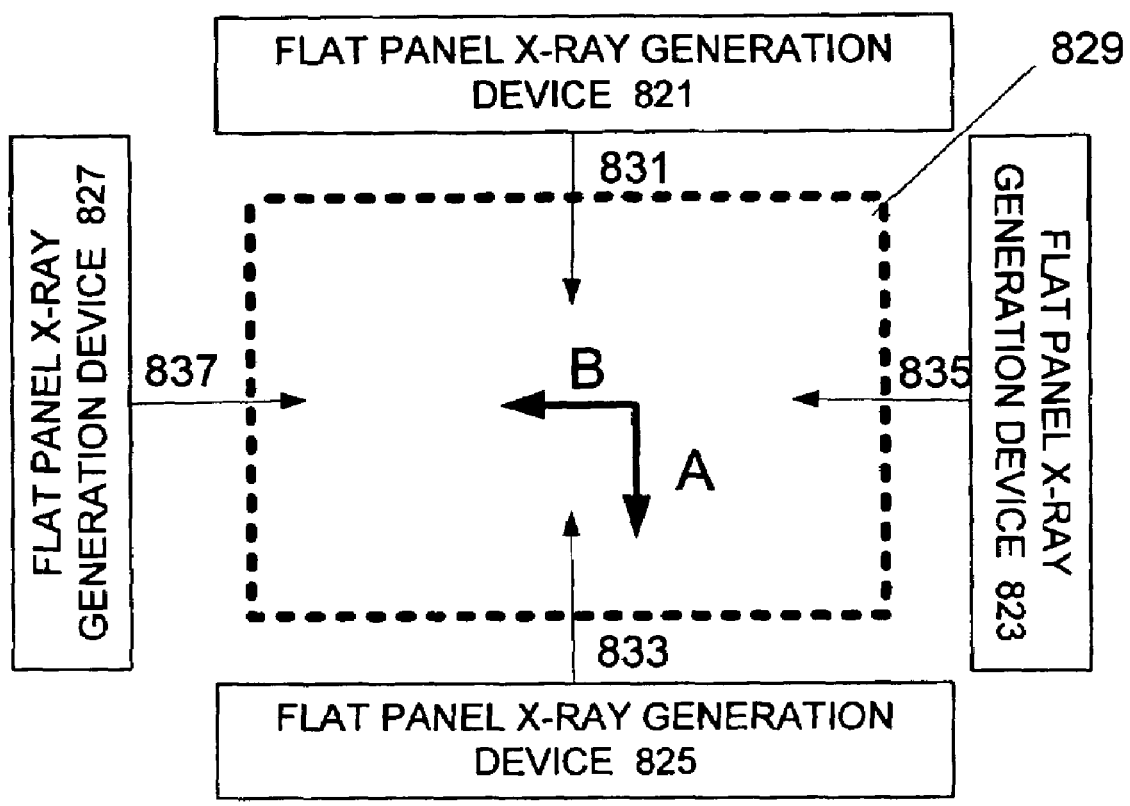
FIG. 8b is a schematic top view of an x-ray treatment system according to an alternative embodiment of the invention, within which two opposing pairs of large area flat panel x-ray sources are used.

FIGS. 8A-8B schematically illustrate alternative irradiation systems for the sanitation and/or decontamination of liquid and/or gaseous materials, omitting the elements other than the x-ray generation devices, radiation, and target zones for ease of understanding. In particular, FIG. 8A shows a system wherein two opposing flat-panel radiation sources as described above are employed. In particular, source 801 is oriented and situated to emit radiation 802 across the target zone 803 in direction A. At the same time a second source 804 is oriented and situated to emit radiation 805 across the target zone 803 in direction B. In this manner, more rapid radiation treatment of material in the target zone 803 may be effected, and the dose becomes become more uniform throughout the irradiated material in the target zone 803. In addition, the power and spacing of the sources 801, 804 may be adjusted to adjust the dose profile within the treated material.

FIG. 8B shows a system wherein two pairs of opposing flat-panel radiation sources as described above are employed. In particular, source 821 is oriented and situated to emit radiation 831 across the target zone 829 in direction A. At the same time source 825 is oriented and situated to emit radiation 833 across the target zone 829 in the opposite direction. In concert, source 823 is oriented and situated to emit radiation 835 across the target zone 829 in direction B, while source 827 is oriented and situated to emit radiation 837 across the target zone 829 in the opposite direction. In this manner, more rapid radiation treatment of material in the target zone 829 may be effected. Also, as described above, the power and spacing of the sources 821, 823, 825, 827 may be adjusted to alter the dose profile within the treated material. It will be appreciated that all target zones according to the illustrated embodiments are three dimensional, having height and width dimensions substantially parallel to the face of the x-ray generation apparatus(es), and a depth dimension substantially perpendicular to the emitted radiation.

In a further embodiment of the invention, the target substance for treatment is a polymerizable chemical, and radiation thereof serves to polymerize the material. This technique improves over prior polymerization systems that use UV radiation rather than the higher energy x-ray radiation. In particular, with x-ray polymerization, thicker sheets may be created. In addition, the system throughput, regardless of sheet thickness, can be improved over prior methods due to the higher energy and faster action of x-ray radiation.

The illustrated arrangements of x-ray sources with respect to number, orientation, and configuration are not exclusive, and any number of other arrangements will be apparent to those of skill in the art given the teachings herein.

Although the foregoing illustrations describe a single pass treatment of material in a radiation treatment system, it will be appreciated that other protocols may be used alternatively or additionally. For example, material may be slowly rotated in the target zone throughout the exposure time. Instead, the target material may be rotated in certain increments at predetermined times. For example, the material may be rotated 180 degrees half way through the radiation period.

In certain embodiments of the invention, the flat source treatment systems described herein improve over existing point source treatment system by increasing dose rate to increase efficiency and product throughout. However, even in embodiments of the invention wherein the inventive systems are used at lower dose rates, they can still provide decreased installation and operational costs over competing systems.

It will be appreciated that a new and useful x-ray treatment system has been described herein. In view of the many possible embodiments to which the principles of this invention may be applied, it should be recognized that the embodiments described herein with respect to the drawing figures are meant to be illustrative only and should not be taken as limiting the scope of invention. For example, those of skill in the art will recognize that the precise configurations and shapes shown are exemplary and that the illustrated embodiments can thus be modified in arrangement and detail without departing from the spirit of the invention.

Therefore, the invention as described herein contemplates all such embodiments as may come within the scope of the following claims and equivalents thereof.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

We claim:

1. A method of irradiating a target substance to reduce biological effects of a contaminant presence in the target substance, the method comprising: providing a source of x-ray radiation having a gated field emitter electron source and two electron targets whereby the electron source emits electrons in at least two opposite directions while the source of x-ray radiation emits x-ray radiation from both electron targets in substantially the same direction, the source of x-ray radiation operating in a reflective and transmissive mode; placing the target substance within a target zone of the source of x-ray radiation; and irradiating the target substance with radiation emitted from the source of x-ray radiation to reduce the biological effects of the contaminant presence in the target substance.

2. The method according to claim 1, wherein the target substance comprises an edible substance.

3. The method according to claim 1, wherein the contaminant is bacterial, fungal, or viral, and wherein reduction of the biological effects of the contaminant presence comprises killing an amount of the contaminant sufficient to substantially reduce a risk of infection in a consumer of the target substance.

4. The method according to claim 1, wherein the contaminant is bacterial, fungal, or viral, and wherein reduction of the biological effects of the contaminant presence comprises killing an amount of the contaminant sufficient to substantially reduce spoilage of the target substance.

5. The method according to claim 1, wherein the contaminant is chemical, and wherein reduction of the biological effects of the contaminant presence comprises chemically modifying an amount of the contaminant sufficient to substantially reduce a risk of a toxic reaction in a consumer of the target substance.

6. The method according to claim 1, wherein irradiating the target substance to reduce biological effects of the contaminant presence in the target substance comprises irradiating the target substance for a predetermined time period at a predetermined dose level.

7. The method according to claim 1, wherein providing a source of x-ray radiation comprises providing multiple flat panel sources of x-ray radiation arranged to irradiate the target zone, and wherein the step of irradiating the target substance further comprises irradiating the target substance with radiation from each of the multiple flat panel sources of x-ray radiation.

8. The method according to claim 1, wherein the electrons provided by the gated field emitter electron source are accelerated toward and impact the electron targets, thereby causing a release of x-ray radiation from the electron targets.

9. The method according to claim 8, wherein the electron targets are positively biased with respect to the electron source.

10. The method according to claim 8, wherein the electron targets are grounded, and the electron source is negatively biased with respect to the electron targets.

11. A treatment system for irradiating a target substance to reduce biological effects of a contaminant presence in the target substance, the treatment system comprising: one or more sources of x-ray radiation, each having two electron targets for receiving oppositely directed electrons while emitting x-ray radiation from both electron targets the same in substantially direction, wherein the one or more sources of x-ray radiation comprise a gated field emitter electron source and operate in a combined reflective and transmissive mode; and a target zone, whereby irradiation of the target substance with the radiation from the one or more sources of x-ray radiation serves to reduce the biological effects of the contaminant presence in the target substance.

12. The system according to claim 11, wherein the target substance comprises an edible substance.

13. The system according to claim 11, wherein the contaminant is bacterial, fungal, or viral, and wherein reduction of the biological effects of the contaminant presence comprises killing an amount of the contaminant sufficient to substantially reduce a risk of infection in a consumer of the target substance.

14. The system according to claim 11, wherein the contaminant is bacterial, fungal, or viral, and wherein reduction of the biological effects of the contaminant presence comprises killing an amount of the contaminant sufficient to substantially reduce spoilage of the target substance.

15. The system according to claim 11, wherein the contaminant is chemical, and wherein reduction of the biological effects of the contaminant presence comprises chemically modifying an amount of the contaminant sufficient to substantially reduce a risk of a toxic reaction in a consumer of the target substance.

16. The system according to claim 11, wherein the one or more sources of x-ray radiation are controlled to radiate the target substance for a predetermined time period at a predetermined dose level.

17. The system according to claim 11, wherein the one or more sources of x-ray radiation comprise multiple sources of x-ray radiation sources arranged such that each irradiates the target zone.

18. The system according to claim 11, wherein the target substance is liquid or gas, the system further comprising a conduit passing through the target zone for conveying the target substance through the target zone, wherein the conduit is substantially transparent to x-ray radiation in at least a portion of the conduit situated within the target zone.

19. A method of irradiating a target substance to polymerize the target substance, the method comprising: providing at least one source of x-ray radiation having a gated field emitter electron source and two electron targets whereby the electron source emits electrons in at least two opposite directions while the source of x-ray radiation emits x-ray radiation from both electron targets in substantially the same direction; the at least one source of x-ray radiation operating in a reflective and transmissive mode; transporting the target substance through a target zone of the at least one source of x-ray radiation; and irradiating the target substance with the radiation from the at least one source of x-ray radiation to polymerize the target substance.

20. A method of irradiating a target substance to reduce biological effects of a contaminant presence in the target substance, the method comprising: providing at least one source of x-ray radiation, wherein the at least one source of x-ray radiation comprises an electron source for providing electrons and two electron targets, whereby the electron source emits electrons in at least two opposing directions while the source of x-ray radiation emits x-ray radiation from both electron targets in substantially the same direction; wherein the electrons provided by the electron source are accelerated toward and impact the two electron targets, thereby causing a release of x-ray radiation from the two electron targets; the at least one source of x-ray radiation in a reflective and transmissive mode; placing the target substance within a zone of the at least one source of x-ray radiation; and irradiating the target substance with radiation emitted from the at least one source of x-ray radiation to reduce the biological effects of the contaminant presence in the target substance.

* * * * *